United States Patent [19]

Testerman et al.

[11] Patent Number: 5,344,438
[45] Date of Patent: Sep. 6, 1994

[54] CUFF ELECTRODE

[75] Inventors: Roy L. Testerman, New Hope; Ralph W. Bierbaum, Coon Rapids, both of Minn.

[73] Assignee: Medtronic, Inc., Minneapolis, Minn.

[21] Appl. No.: 48,591

[22] Filed: Apr. 16, 1993

[51] Int. Cl.$^5$ .............................................. A61N 1/05
[52] U.S. Cl. ................................... 607/118; 128/642
[58] Field of Search ......................... 128/642; 607/118

[56] References Cited

U.S. PATENT DOCUMENTS

| | | |
|---|---|---|
| 26,809 | 10/1866 | Hagfors . |
| 1,662,446 | 3/1928 | Wappler . |
| 3,157,181 | 11/1964 | McCarty . |
| 3,405,715 | 10/1968 | Hagfors . |
| 3,421,511 | 1/1969 | Schwartz . |
| 3,654,933 | 4/1972 | Hagfors . |
| 3,738,368 | 6/1973 | Avery . |
| 3,774,618 | 11/1973 | Avery . |
| 3,822,708 | 7/1974 | Zilber . |
| 3,955,560 | 5/1976 | Stein . |
| 4,245,645 | 1/1981 | Arnseneault . |
| 4,284,085 | 8/1981 | Hansen . |
| 4,341,221 | 7/1982 | Testerman . |
| 4,573,481 | 3/1986 | Bullara . |
| 4,602,624 | 7/1986 | Naples . |
| 4,649,939 | 3/1987 | Curtis . |
| 4,934,368 | 6/1990 | Lynch . |
| 4,940,065 | 7/1990 | Tanagho . |
| 4,979,511 | 12/1990 | Terry, Jr. . |
| 5,038,781 | 8/1991 | Lynch . |
| 5,092,332 | 3/1992 | Lee et al. . |
| 5,095,905 | 3/1992 | Klepinski . |
| 5,143,067 | 9/1992 | Rise et al. . |
| 5,158,097 | 10/1992 | Christlieb . |
| 5,265,608 | 11/1993 | Lee et al. ........................... 128/642 |

OTHER PUBLICATIONS

"A Nerve Cuff Technique for Selective Excitation of Peripheral Nerve Trunk Regions" by James D. Sweeney, IEE Transactions on Biomedical Engineering vol. 37 No. 7 Jul. 1990.

"Selective Activation of Muscles Using Peripheral Nerve Electrodes" by McNeal et al., Med. & Biol. Eng. & Comput., 1985, 23, 249–253.

"Design and Evaluation of Nerve Stimulating Electrodes", by Roy L. Testerman, et al. Medical Research Engineering, vol. 10, No. 1, 1971.

"Clinical Experience with a Helical Bipolar Stimulating Lead", by Tarver et al., Pace, vol. 15, Oct. 92.

"Light and Electron Microscopic Studies of Phrenic Nerves After Long-Term Electrical Stimulation", by Kim et al., Journal of Neurosurgery 58(1):84–91 Jan. 1983.

*Primary Examiner*—Lee S. Cohen
*Attorney, Agent, or Firm*—Harold R. Patton; Daniel W. Latham

[57] ABSTRACT

A half-cuff electrode for mounting on a nerve comprising a hollow, semi-cylindrical body of nonconductive material having an open, U-shaped cross section with an interior base portion of the U-shaped cross section adapted to fit closely about a selected portion of the circumference of the nerve. The electrode may be secured in contact with the selected portion of the nerve by placing the nerve within the open, base portion of the body and applying to at least one leg of the U-shaped body a biasing force sufficient to retain the nerve within the body base portion. Since the electrode has a half-cuff design and the method used for securing it to the nerve leaves one side of the half-cuff open, the nerve is able to swell without compromising the circulation of nutrients through the nerve tissue. Preferably, in an additional step to minimize trauma to the nerve, the electrode also includes a resilient support extending from the body of the electrode which is used to secure the device without the application of excessive biasing forces to the nerve.

17 Claims, 2 Drawing Sheets

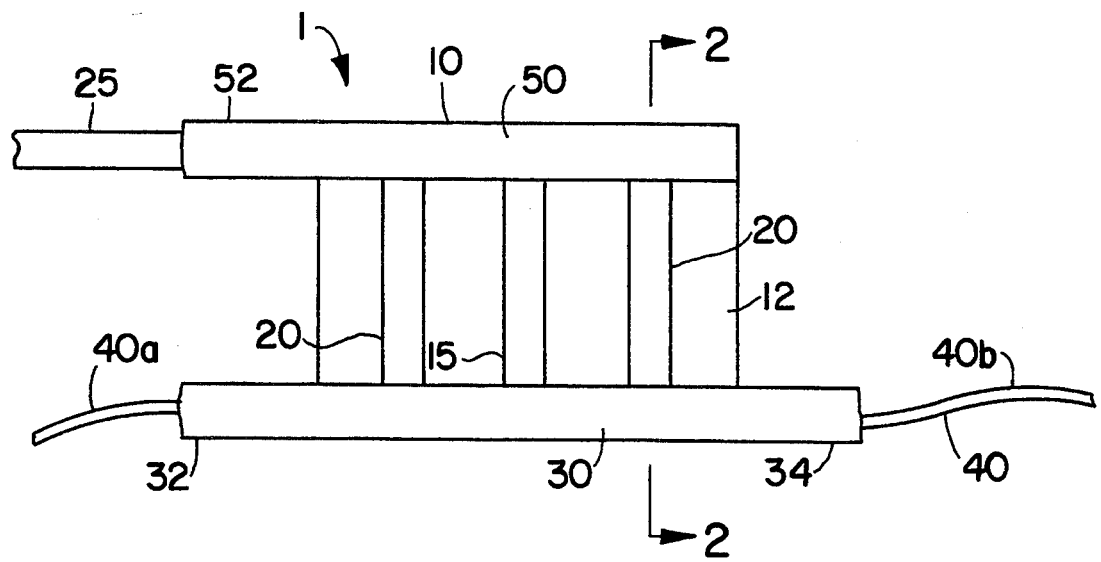
F I G. 1
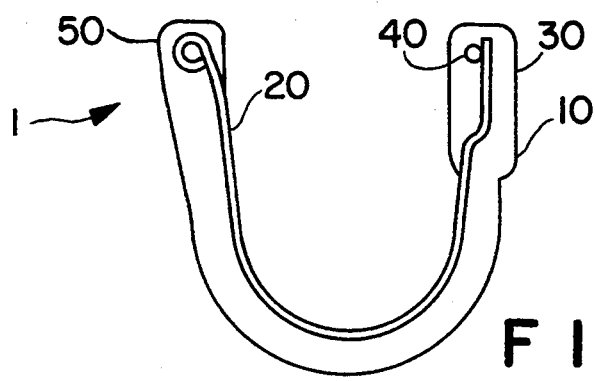
F I G. 2
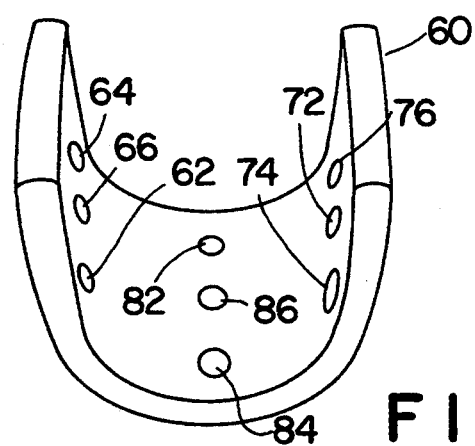
F I G. 3

CUFF ELECTRODE

BACKGROUND OF THE INVENTION

The present invention relates generally to implantable medical electronic devices and more specifically to electrodes for nerve stimulation.

Many peripheral nerves contain fascicles which innervate antagonistic muscles. For example, the hypoglossal nerve contains fascicles innervating the genioglossus muscle which extends the tongue, and also the styloglossus muscle which retracts the tongue. In addition, many nerves to be stimulated are near other structures which must not be stimulated. Therefore, it is desirable to have an electrode array which limits the stimulus current to selected nerve fascicles.

Cuff electrodes for recording neural signals and stimulating nerve tissue are well known. For example, U.S. Pat. No. 3,774,618 issued to Avery discloses a thin, flexible strip of plastic having lead wires encapsulated in the plastic which is implanted by wrapping the plastic strip and lead wires around a single nerve.

It has also been known that a tripolar electrode arrangement confines stimulus current to the nerve cuff and that a tripolar arrangement is more selective than a monopolar arrangement (see e.g. Testerman et al., Design and Evaluation of Nerve Stimulating Electrodes, *Med Res Eng* 10: 6–11 1971; and Sweeney et al., A nerve cuff technique for selective excitation of peripheral nerve trunk regions, *IEEE Trans Biomed Eng* 37: 706–715, 1990). This selectivity can be enhanced with one or more "steering" electrodes. The electrode must also be in close contact with the nerve in order for the selectivity to work (see e.g. McNeil et al., Selective activation using peripheral nerve electrodes, *Med & Biol Eng & Comput* 23: 249–253, 1985). Several self-sizing cuff electrode designs have been proposed (e.g. U.S. Pat. Nos. 4,573,481; 4,602,624; and 5,095,905) but these designs tend to be fragile and difficult to install. Also important in cuff electrode design is to avoid trauma to the nerve. A half cuff design to minimize phrenic nerve trauma has been disclosed in Kim et al., Light and electron microscope studies of phrenic nerves after long-term electrical stimulation, *J Neurosurg* 58: 84–91, 1983.

It is therefore an object of the present invention to provide an electrode for selectively stimulating nerve fascicles.

It is also an object of the present invention to provide an electrode which is easy to secure onto a peripheral nerve.

It is also an object of the present invention to provide an electrode which minimizes trauma to the nerve.

SUMMARY OF THE INVENTION

We have discovered a half-cuff electrode for mounting on a nerve comprising a hollow, semi-cylindrical body of nonconductive material having an open, U-shaped cross section with an interior base portion of the U-shaped cross section adapted to fit closely about a selected portion of the circumference of the nerve. The electrode includes a conductive material mounted on the interior base portion of the body which is adapted for contact with a portion of the nerve and also includes lead wires in electrical contact with the conductive material.

The means for securing the electrode is unique in that it is secured in contact with the selected portion of the nerve by placing the nerve within the open, base portion of the body and applying to at least one leg of the U-shaped body a biasing force sufficient to retain the nerve within the body base portion. This biasing force can be supplied by suturing the electrode to an attachment point on tissue adjacent the nerve. Since the electrode has a half-cuff design and the method used for securing it to the nerve leaves one side of the half-cuff open, only a selected portion of the circumference of the nerve is stimulated and the nerve is able to swell without compromising the circulation of nutrients through the nerve tissue. Preferably, in an additional step to minimize trauma to the nerve, the electrode also includes a resilient support extending from the body of the electrode which is used to secure the device without the application of excessive biasing forces to the nerve. For additional convenience in implantation, the suture can be incorporated as an integral part of the electrode extending from the resilient support or it can even be slideably inserted through an aperture extending between two resilient supports so that it can be secured to adjacent tissue at both ends. This slidable suture method of attachment allows the position of the electrode to be adjusted slightly after the sutures are tacked in place. At the other leg of the electrode, the lead and lead insulator can also be used as a structure to secure the electrode to the nerve, thus forming a three point attachment to the nerve. The lead and lead insulator are simply sutured to an attachment point on an adjacent tissue. Again, a resilient mounting point for the lead and lead insulator can be used to relieve stress on the nerve.

The electrode can include both active electrodes and current guarding electrodes on the interior base portion of the electrode body in order to improve selectivity and minimize current leakage during stimulation. Suitable active electrode and current guarding electrode arrangements are disclosed in U.S. Pat. No. 3,654,933 issued to Hagfors which is incorporated herein by reference in its entirety. In one preferred electrode arrangement, there are three flat rectangular strips of metal that serve as electrodes in which the central electrode is the active electrode and the outboard electrodes are the current guarding electrodes. Another possible electrode arrangement is to place a number of small button electrodes on the contacting portion of the cuff electrode that can be selectively employed as active electrodes or current guarding electrodes in order to provide the desired steering of stimulation to appropriate portion of the nerve.

BRIEF DESCRIPTION OF THE DRAWINGS

FIG. 1 is a top plan view of an electrode according to the present invention.

FIG. 2 is a cross sectional view of the electrode of FIG. 1.

FIG. 3 is a partial perspective view of an electrode according to the present invention showing an alternative electrode configuration.

DETAILED DESCRIPTION OF THE INVENTION

Figure 4:
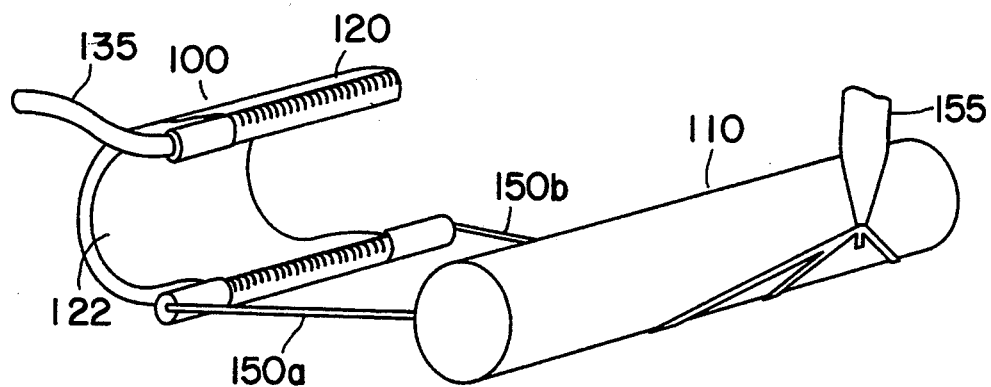
FIG. 4 is a perspective view of an electrode according to the present invention being placed around a nerve.

Referring now to the drawing figures, FIGS. 1 and 2 show an electrode 1 according to the present invention. The electrode 1 has a body 10 of nonconductive material having a generally semi-cylindrical shape and an open, generally U-shaped cross section. At the interior base portion 12 of the body 10 are electrodes 15, 20 of conductive material, including an active electrode 15 and two current guarding electrodes 20 on either side of the active electrode 15. A lead 25 extends from the body 10 which contains lead wires (not shown) which electrically connect with the conductive material of the electrodes 15, 20.

The electrode 1 also includes means for securing the electrode 1 in contact with a nerve on one leg 30 of the electrode 1 in the form of a suture 40 which extends through leg 30 and includes ends 40a, 40b. By slipping the electrode 1 base portion 12 over a nerve and tying the suture ends 40a, 40b to tissues adjacent the nerve to maintain a biasing force between the nerve and the electrode 1, the nerve is retained within the base portion 12. Also shown are supports 32, 34 at each end of leg 30 which are made of a resilient material which allow them to flex in response to excess tension on the suture ends 40a, 40b. The electrode 1 also has means for securing the electrode 1 at its second leg 50 since the lead 25 can also be tied to adjacent tissue to provide a biasing force on the second leg 50. A support 52 of resilient material is also provided to prevent excess tension on the nerve from the lead 25 and the lead 25 may also be coiled (not shown) to keep tension applied to the lead 25 from being transmitted to the electrode 1.

Referring now to FIG. 3, a portion of a cuff electrode 60 according to the present invention is shown in perspective with an alternative electrode arrangement which applies steering principles. If button electrodes 62 and 64 are the only electrodes connected as an anode and electrode 66 is the only electrode connected as a cathode, then the current will tend to be confined to the left side of the cuff electrode 60. If electrode 72 is also then connected as an anode, the current is then even more completely confined to the left side of the cuff electrode 60. Similarly, if button electrodes 74 and 76 are the only electrodes connected as an anode and electrode 72 is the only electrode connected as a cathode, then the current will tend to be confined to the right side of the cuff electrode 60. If electrode 66 is then also connected as an anode, then the current is even more completely confined to the right side of the electrode cuff 60. If only electrodes 82 and 84 are anodes, and only electrode 86 is the only cathode, then the current tends to be confined to the base portion of the cuff electrode 60. Also, using electrode 66 or electrode 72 as steering anodes tends to confine the current to the lower right or lower left quadrants of the cuff electrode 60 respectively.

Figure 5:
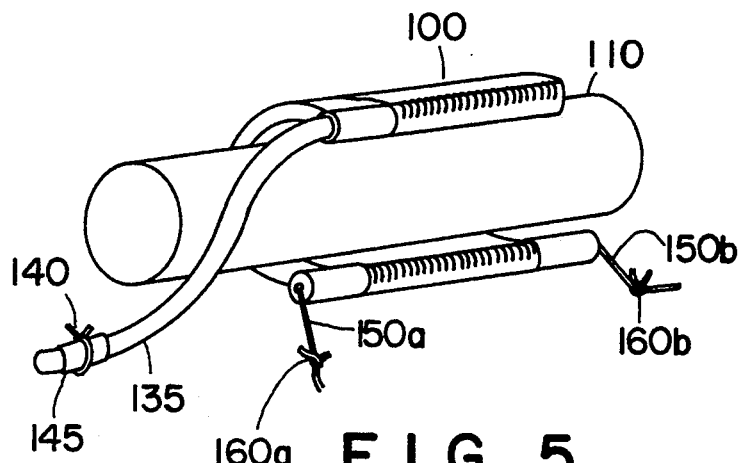
FIG. 5 is a perspective view of the electrode of FIG. 3 in which the electrode has been placed about the nerve and secured by sutures to adjacent tissue.
Figure 6:
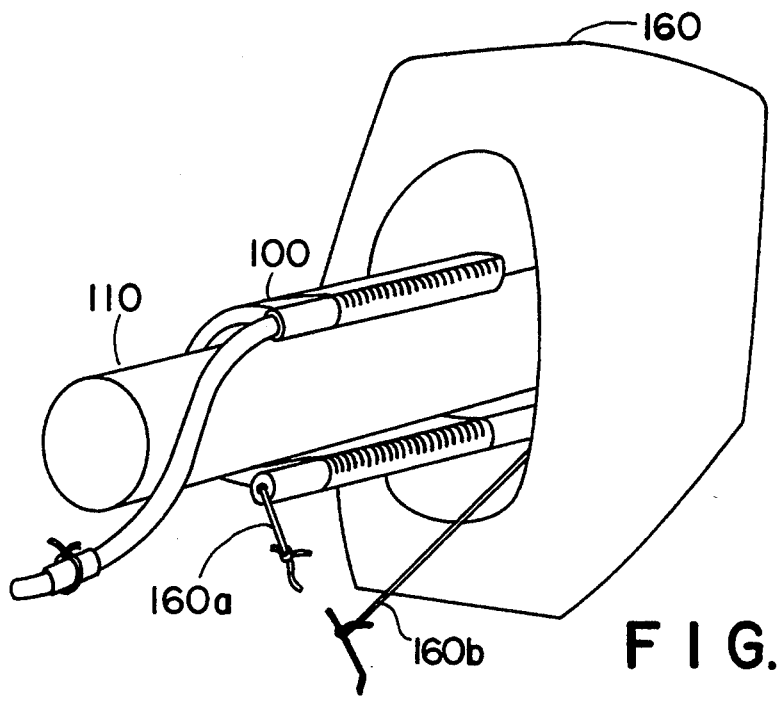
FIG. 6 is a perspective view of an electrode according to the present invention and its placement into a foramen.

Referring now to FIGS. 4 and 5, a method for securing an electrode 100 to a nerve 110 is shown. The electrode 100 again includes a body 120 with a generally semi-cylindrical shape and a U-shaped cross section and an interior base portion 122. Electrodes (not shown) are in the interior base portion 122.

When securing the electrode 100 to the nerve 110, the suture ends 150a, 150b are brought under the nerve 110 that has been carefully isolated from adjacent tissue (not shown) and with a forceps 155 are drawn under the nerve 110 until the nerve is seated in the interior base portion 122. While maintaining a slight tension on the suture ends 150a, 150b to retain the electrode 100 on the nerve 110, they are tacked to adjacent tissue (not shown) with knots 160a, 160b. Optionally, lead 135 is also secured to adjacent tissue (not shown) by tying a suture 140 around the lead 135. To prevent damage to the lead 135, the suture 140 is not applied directly to the lead 135 but is instead placed on an anchor cuff 145 around the lead 135. The electrode 100 so secured remains open to limit the application of a stimulatory signal to a portion of the nerve 110 and to permit the nerve 110 to swell. Both right and left hand versions of the electrode 100 can be made to accommodate the requirements of the particular nerve and surrounding tissues.

Referring now to FIG. 5, the electrode 100 is shown attached to nerve 110 as set forth above. By adjusting the relative position of the suture ends 160a, 160b and the electrode 100 by sliding them through the electrode 100, the electrode 100 can be moved slightly such that it can be inserted into a foramen 160.

Referring again to the electrode 1 shown in FIGS. 1 and 2, only a few conventionally available materials and processes are needed to make the electrode 1. The nonconductive material of the body 10 can be, for example, molded silicone rubber and silicone tubing can be used for the insulator for the lead 25, while the electrodes 15, 20 can be made from platinum ribbon and the wires to the lead 25 can be bundled, stranded MP-35N wire with PTFE insulation. The assembly of such an electrode 1 is straightforward and basically includes making an electrode subassembly by welding lead wires onto the platinum ribbon and securing silicone tubing as insulating spacers between the platinum ribbon elements with silicone adhesive; making a silicone rubber preform for the body 10 by injection molding; then combining the electrode assembly with the silicone rubber preform (and also a piece of silicone rubber tubing to make a passageway for the suture 40 and any other reinforcement members such as a polymeric mesh that might be used to reinforce the silicone rubber) in a mold; and curing the silicone rubber body 10 with the included parts in the mold to make a finished electrode 1.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. An electrode apparatus for mounting on a nerve comprising:
   (a) a hollow, semi-cylindrical body of nonconductive material having an open, U-shaped cross section sized in both width and depth to seat the entire diameter of the nerve therewithin with an interior base portion of the U-shaped cross section adapted to fit closely about a selected portion of the circumference of the nerve;
   (b) a conductive material mounted on the interior base portion of the body and adapted for contact with the nerve;
   (c) a lead wire in electrical contact with the conductive material; and (d) means for securing the electrode apparatus in contact with the selected portion of the nerve by placing the nerve within the U-shaped cross section of the body and applying to at least one leg of the U-shaped body a biasing force sufficient to retain the nerve within the body base portion without causing the U-shaped cross section to close around the nerve.

2. An electrode apparatus according to claim 1 wherein the means for securing the electrode apparatus includes at least one suture.

3. An electrode apparatus according to claim 1 wherein the means for securing the electrode apparatus also includes a resilient support extending from the body of nonconductive material.

4. An electrode apparatus according to claim 3 wherein a suture extends from the resilient support for attachment to tissue.

5. An electrode apparatus according to claim 4 wherein the suture is integral with the resilient support.

6. An electrode apparatus according to claim 5 wherein the means for securing the electrode apparatus includes a pair of resilient supports with an aperture extending therebetween and the suture material slidably extending through the aperture.

7. An electrode apparatus according to claim 1, 2, or 3 wherein the lead wire extends from a second leg of the U-shaped body and is attached to suture means for attachment to tissue.

8. An electrode apparatus according to claim 7 wherein the lead wire is connected to the second leg by a resilient structure.

9. An electrode apparatus for mounting on a nerve comprising:
(a) a hollow, semi-cylindrical body of nonconductive material having an open, U-shaped cross section sized in both width and depth to seat the entire diameter of the nerve therewithin with an interior base portion of the U-shaped cross section adapted to fit closely about a selected portion of the circumference of the nerve;
(b) a conductive material mounted on the interior base portion of the body and adapted for contact with the nerve, the conductive material comprising at least one active electrode and at least one current guarding electrode;
(c) a lead wire in electrical contact with the conductive material at the active electrode and a lead wire in electrical contact with the conductive material at the current guarding electrode; and
(d) means for securing the electrode apparatus in contact with the selected portion of the nerve by placing the nerve within the U-shaped cross section of the body and applying to at least one leg of the U-shaped body a biasing force sufficient to retain the nerve within the body base portion without causing the U-shaped cross section to close around the nerve.

10. An electrode apparatus according to claim 9 wherein each electrode is a flat, rectangular strip.

11. An electrode apparatus according to claim 9 wherein each electrode is a button contact.

12. An electrode apparatus according to claim 9 wherein the active electrode is centrally located between current guarding electrodes.

13. An electrode apparatus according to claim 9 wherein the conductive material also provides a steering electrode.

14. A method for securing an electrode to a nerve comprising the steps of:
(a) sliding a U-shaped electrode around the nerve such that the entire diameter of the nerve is seated within the electrode; and
(b) applying a sufficient biasing force to at least one leg of the electrode to retain the electrode on the nerve without causing the U-shaped cross section to close around the nerve.

15. The method according to claim 14 wherein the step of applying a biasing force is accomplished by suturing the leg of the electrode to at least one attachment point on tissue adjacent the nerve.

16. A method for securing an electrode to a nerve comprising the steps of:
(a) stringing a suture having a first end and a second end through an aperture in one leg of a U-shaped electrode;
(b) sliding the U-shaped electrode around the nerve such that the nerve is seated on the electrode; and
(c) securing the suture at its first end and at a first attachment point on tissue adjacent the nerve and at its second end to a second attachment point on tissue adjacent the nerve.

17. The method according to claim 16 also comprising the step of sliding the electrode into a foramen.

* * * * *